(12) United States Patent
Bennett et al.

(10) Patent No.: US 8,179,526 B2
(45) Date of Patent: May 15, 2012

(54) SPECTROSCOPIC APPARATUS WITH DISPERSIVE DEVICE FOR COLLECTING SAMPLE DATA IN SYNCHRONISM WITH RELATIVE MOVEMENT OF A FOCUS

(75) Inventors: Robert Bennett, Oakham (GB); Ian P. Hayward, Warminster (GB); Brian J. E. Smith, Dursley (GB)

(73) Assignee: Renishaw PLC, Wotton-Under-Edge ( * ) Notice: Subject to any disclaimer, the term of this patent is extended or adjusted under 35 U.S.C. 154(b) by 394 days.

(21) Appl. No.: 12/458,815

(22) Filed: Jul. 23, 2009

(65) Prior Publication Data

US 2009/0310132 A1     Dec. 17, 2009

Related U.S. Application Data

(63) Continuation-in-part of application No. PCT/GB2009/000214, filed on Jan. 26, 2009, and a continuation-in-part of application No. PCT/GB2008/000252, filed on Jan. 25, 2008.

(30) Foreign Application Priority Data

Jan. 25, 2007 (GB) .................................. 0701477.2
Feb. 29, 2008 (GB) .................................. 0803798.8

(51) Int. Cl.
    *G01J 3/44* (2006.01)
(52) U.S. Cl. ........................................ 356/301; 356/317
(58) Field of Classification Search .................. 356/301, 356/317, 318
    See application file for complete search history.

(56) References Cited

U.S. PATENT DOCUMENTS

| | | | |
|---|---|---|---|
| 3,625,613 A | 12/1971 | Abell et al. |
| 3,733,131 A | 5/1973 | Mould |
| 3,853,404 A | 12/1974 | Barrett |
| 3,914,055 A | 10/1975 | Wolga et al. |
| 3,999,854 A | 12/1976 | Barrett |

(Continued)

FOREIGN PATENT DOCUMENTS

DE     29 35 812 A1     3/1981
(Continued)

OTHER PUBLICATIONS

"Holographic Interference Notch Filters for Raman Spectroscopy," Kaiser Optical Systems, Inc., Feb. 1991, pp. 1-3.
(Continued)

*Primary Examiner* — Layla Lauchman
(74) *Attorney, Agent, or Firm* — Oliff & Berridge, PLC

(57) ABSTRACT

In a Raman spectroscopy apparatus, exciting light is focussed on a sample (26) as a line focus 38. Spectra from points in the line focus are dispersed in rows 46 on a CCD detector 34, having a two-dimensional array of pixels. The line focus moves longitudinally in a direction Y (arrow 48) relative to the sample. Simultaneously and synchronously, charge is shifted in a parallel direction Y' (arrow 50) within the CCD, so that data from a given point in the sample continues to accumulate. This ensures that the data from each sample point arises from illumination which is integrated along the line focus, and makes it easier to stitch the data together subsequently to form an image of the sample. In order to provide averaging in the X direction during fast, low resolution scanning, the line focus is swept across the sample in a zig-zag fashion, between boundary lines 60.

22 Claims, 4 Drawing Sheets

U.S. PATENT DOCUMENTS

| | | | |
|---|---|---|---|
| 4,030,827 | A | 6/1977 | Delhaye et al. |
| 4,081,215 | A | 3/1978 | Penney et al. |
| 4,195,930 | A | 4/1980 | Delhaye et al. |
| 4,397,556 | A | 8/1983 | Müller |
| 4,586,819 | A | 5/1986 | Tochigi et al. |
| 4,648,714 | A | 3/1987 | Benner et al. |
| 5,011,284 | A | 4/1991 | Tedesco et al. |
| 5,112,127 | A | 5/1992 | Carrabba et al. |
| 5,153,670 | A | 10/1992 | Jannson et al. |
| 5,164,786 | A | 11/1992 | Delhaye et al. |
| 5,166,813 | A | 11/1992 | Metz |
| 5,173,748 | A | 12/1992 | Bilhorn |
| 5,442,438 | A | 8/1995 | Batchelder et al. |
| 5,689,333 | A | 11/1997 | Batchelder et al. |
| 5,754,291 | A * | 5/1998 | Kain .............................. 356/318 |
| 7,265,828 | B2 | 9/2007 | Levine |
| 2002/0039186 | A1 | 4/2002 | Rosenberg |
| 2003/0048933 | A1* | 3/2003 | Brown et al. ............... 250/461.2 |
| 2005/0006595 | A1* | 1/2005 | Goodwin et al. ........... 250/458.1 |
| 2010/0097603 | A1 | 4/2010 | Smith |

FOREIGN PATENT DOCUMENTS

| | | |
|---|---|---|
| DE | 40 17 317 A1 | 12/1991 |
| EP | 0 324 583 A3 | 7/1989 |
| EP | 0 407 773 A2 | 1/1991 |
| EP | 0 442 206 A2 | 8/1991 |
| EP | 0 465 350 A1 | 1/1992 |
| EP | 0 502 752 B1 | 9/1992 |
| FR | 2130269 | 11/1972 |
| GB | 1 345 642 | 1/1974 |
| GB | 1 577 198 | 10/1980 |
| GB | 2 241 350 A | 8/1991 |
| JP | A 53-47892 | 4/1978 |
| JP | A 60-53834 | 3/1985 |
| JP | A 60-174934 | 9/1985 |
| JP | A 62-269048 | 11/1987 |
| JP | A 3-116004 | 5/1991 |
| WO | WO 90/07108 | 6/1990 |
| WO | WO 91/11703 | 8/1991 |
| WO | WO 92/17806 | 10/1992 |
| WO | WO 2008/090350 A1 | 7/2008 |
| WO | WO 2008/135766 A1 | 11/2008 |

OTHER PUBLICATIONS

Pelletier et al., "Characterization of Holographic Band-Reject Filters Designed for Raman Spectroscopy," Applied Spectroscopy, vol. 45, No. 5, 1991, pp. 765-769.

Denton et al., "Charge-Injection and Charge-Coupled Devices in Practical Chemical Analysis," American Chemical Society, 1983, pp. 133-152.

Insight Brochure, Meridian Instruments, Inc., 1991.

Treado et al., "Hadamard Transform Raman Imaging," Applied Spectroscopy, vol. 42, No. 5, 1988, pp. 897-901.

Treado et al., "Hadamard Transform Raman Microscopy of Laser-Modified Graphite Electrodes," Applied Spectroscopy, vol. 44, No. 8, 1990, pp. 1270-1275.

Govil et al., "Optical Sectioning Raman Microscopy," Applied Spectroscopy, vol. 45, No. 10, 1991, pp. 1604-1606.

Flaugh et al., "Development of a New Optical Wavelength Rejection Filter: Demonstration of its Utility in Raman Spectroscopy," Applied Spectroscopy, Vo. 38, No. 6, 1984, pp. 847-850.

Asher et al., "Crystalline Colloidal Bragg Diffraction Devices: the Basis for a New Generation of Raman Instrumentation," Spectroscopy, vol. 1, No. 12, 1986, pp. 26-31.

Batchelder, "Multichannel Raman Spectroscopy with a Cooled CCD Imaging Detector," ESN-European Spectroscopy News, vol. 80, 1988, pp. 28, 32 and 34.

Delhaye et al., "Raman Microprobe and Microscope with Laser Excitation," Journal of Raman Spectroscopy, vol. 3, 1975, pp. 33-43.

Karger et al., "Laser Raman Spectrometer for Process Control," Applied Optics, vol. 12, No. 9, Sep. 1973, pp. 2083-2087.

Gajda et al., "Optical Determination of Crystal Axis Orientation in Silicon Fragments," IBM Technical Disclosure Bulletin, vol. 27, No. 7A, Dec. 1984, pp. 3865-3866.

Duncan et al., "Imaging biological compounds using the coherent anti-Stokes Raman scattering microscope," Optical Engineering, vol. 24, No. 2, Apr. 1985, pp. 352-355.

Dhamelincourt, "Laser Molecular Microscope," Lasers in Chemistry, 1977, pp. 48-53.

"Raman Holographic Edge Filters," Physical Optics Corp., Torrance, CA.

"Holographic Notch Filter," Kaiser Optical Systems, Inc., Ann Arbor, MI.

Pitt, "Raman shifts into industry," Physics World, Oct. 1991, pp. 19-20.

Deckert et al., "Scanning Multichannel Technique for Improved Spectrochemical Measurements with a CCD Camera and its Application to Raman Spectroscopy," Applied Spectroscopy, vol. 46, No. 2, 1992, pp. 322-328.

Knoll et al., "Improving Spectroscopic Techniques by a Scanning Multichannel Method," Applied Spectroscopy, vol. 44, No. 5, 1990, pp. 776-782.

Carrabba et al., "The Utilization of a Holographic Bragg Diffraction Filter for Rayleigh Line Rejection in Raman Spectroscopy," Applied Spectroscopy, vol. 44, No. 9, 1990, pp. 1558-1561.

Yang et al., "Holographic Notch Filter for Low-Wavenumber Stokes and Anti-Stokes Raman Spectroscopy," Applied Spectroscopy, vol. 45, No. 9, 1991, pp. 1533-1536.

Liu et al., "Multispectral Hadamard Transform Raman Microscopy," Applied Spectroscopy, vol. 45, No. 10, pp. 1717-1720, 1991.

Owen, "Holographic notch filter (HNF)," Proceedings Reprint, Computer and Optically Generated Holographic Optics, SPIE—The International Society for Optical Engineers, vol. 155, Jul. 24-25, 1991.

Puppels et al., "A high-throughput Raman notch filter set," Rev. Sci. Instrum., vol. 61, No. 12, Dec. 1990, pp. 3709-3712.

Laude, "Spectrometre a Deux Fabry-Perot Asservis," Journal de Physique, vol. 28, Nos. 3-4, Mar.-Apr. 1967, pp. C2-322-C2-325. (with English-language abstract).

Rich et al., "Lippmann Volume Holographic Filters for Rayleigh Line Rejection in Raman Spectroscopy," Practical Holography V, SPIE, vol. 1461, pp. 2-7, 1991.

Schrader, "Fortschritte in der Technik der Ramanspektroskopie," Chemie-Ingenieur Technik, vol. 17, 1967.

Bergin, "A microscope for Fourier Transform Raman spectroscopy," Spectrochimica Acta, vol. 46A, No. 2, 1990, pp. 153-159.

Dyer et al.; "Application of Continuous Extended Scanning Techniques to the Simultaneous Detection of Raman Scattering and Photoluminescence from Calcium Disilicates using Visible and Near-Infrared Excitation;" Journal of Raman Spectroscopy; vol. 26, pp. 777-785, 1995.

Pommier et al.; "Array Detectors for Raman Spectroscopy;" *Handbook of Vibrational Raman Spectroscopy*; 2002; pp. 1-15; John Wiley & Sons, Ltd.

U.S. Appl. No. 08/854,141, filed May 9, 1997 in the name of Batchelder et al.

U.S. Appl. No. 08/574,929, filed Dec. 19, 1995 in the name of Batchelder et al.

International Search Report issued in PCT/GB2008/001582, mailed Aug. 8, 2008.

Written Opinion issued in PCT/GB2008/001582, mailed Aug. 8, 2008.

International Search Report issued in PCT/GB2009/000214, mailed May 8, 2009.

Written Opinion issued in PCT/GB2009/000214, mailed May 8, 2009.

International Search Report issued in PCT/GB2008/000252, mailed Jun. 26, 2008.

Written Opinion issued in PCT/GB2008/000252, mailed Jun. 26, 2008.

Bowden et al; "Line-Scanned Micro Raman Spectroscopy Using a Cooled CCD Imaging Detector;" *Journal of Raman Spectroscopy*;

1990; pp. 37-41; vol. 21, No. 1; John Wiley & Sons, Ltd., United Kingdom.

Pitt et al; "Engineering Aspects and Applications of the New Raman Instrumentation," *IEE Proceedings—Science, Measurement and Technology*; Nov. 2005; pp. 241-318; vol. 152, No. 6; IEE, United Kingdom.

Lankers et al; A Device for Surface-Scanning Micro-Raman Spectroscopy; *Applied Spectroscopy*; Sep. 1992; pp. 1331-1334; vol. 46, No. 9; The Society for Applied Spectroscopy, Baltimore, MD, U.S.A.

Feb. 3, 2012 Office Action issued in U.S. Appl. No. 12/450,520.

* cited by examiner

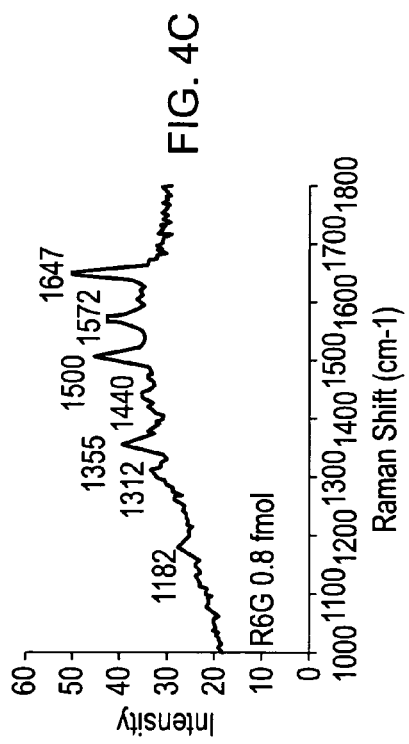
FIG. 4C
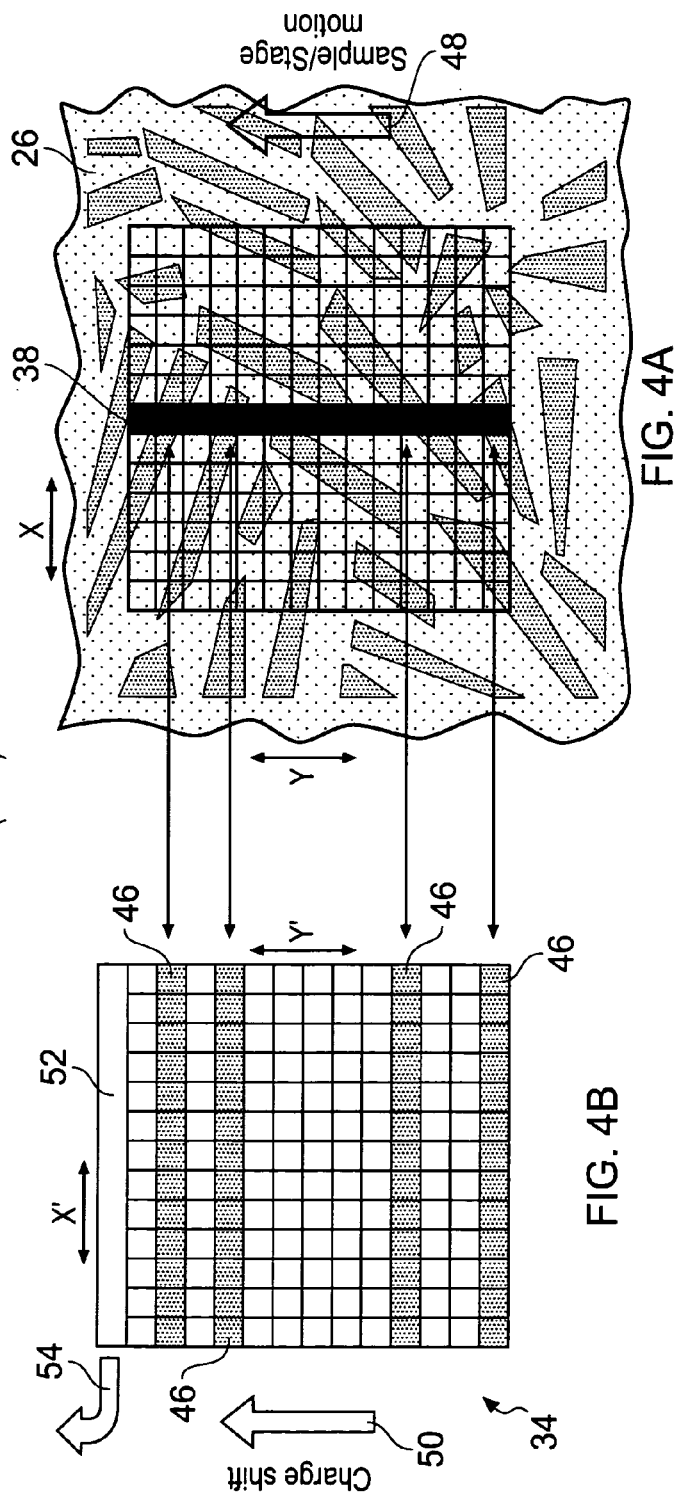
FIG. 4A
FIG. 4B

SPECTROSCOPIC APPARATUS WITH DISPERSIVE DEVICE FOR COLLECTING SAMPLE DATA IN SYNCHRONISM WITH RELATIVE MOVEMENT OF A FOCUS

FIELD OF THE INVENTION

This invention relates to spectroscopic apparatus and methods. It is particularly useful in Raman spectroscopy, though it can equally be used in other forms of spectroscopy, e.g. using fluorescence, narrow-line photoluminescence or cathodoluminescence.

DESCRIPTION OF PRIOR ART

An example of Raman spectroscopic apparatus is shown in U.S. Pat. No. 5,442,438 (Batchelder et al). Light from a laser source is focussed to a spot on a sample. Interaction between the light and the molecules of the sample causes Raman scattering into a spectrum having frequencies and wavenumbers which are shifted relative to the exciting laser frequency. After filtering out the laser frequency, a dispersive device such as a diffraction grating disperses this scattered Raman spectrum across a two-dimensional photodetector array, e.g. in the form of a charge-coupled device (CCD). Different molecular species have different characteristic Raman spectra, and so the effect can be used to analyse the molecular species present. The Raman spectrum can also give other information, such as the local stresses or strains in the sample. The photodetector array may for example take the form of a charge-coupled device (CCD) having an array of pixels in which charge accumulates in proportion with the. light received.

If it is desired to map an area of the sample, rather than just a single point, then it is known to mount the sample on a stage which can be moved in orthogonal directions X,Y. Alternatively, movable mirrors may deflect the light beam across the surface of the sample in X and Y directions. Thus, a raster scan of the sample can take place, giving Raman spectra at each point in the scan.

At each point in such a raster scan, the laser beam should illuminate the sample for a sufficient length of time to allow a Raman spectrum to be acquired. Obtaining a map over a large area of the sample can therefore be time consuming.

It is therefore known to illuminate the sample not with a point focus, but with a line focus. This enables the acquisition of spectra from multiple points within the line simultaneously. On the CCD detector, it is arranged that an image of the line extends orthogonally to the direction of spectral dispersion. This enables efficient use of the two-dimensional nature of the detector to acquire the multiple spectra simultaneously. The multiple spectra are formed simultaneously in multiple rows or columns of the CCD array.

One problem with such a line focus arrangement is that inevitably the illuminating laser light will have different intensities at different positions along the line. The resulting spectra from the different positions within the line are therefore not normalised relative to each other and are difficult to compare directly.

Where a large area of the sample is to be mapped, it is also quite likely that the length of the line will be only a fraction of the width or depth of the area to be mapped. Consequently, even such a line focus must undertake a raster scan, in a series of successive stripes. When assembling the resulting stripes into a two-dimensional map of the area, there are difficulties in seamlessly stitching together the data at the ends of the line focus.

These difficulties in stitching the data together have several different causes. One cause is the above difference in intensity at different positions along the line focus. Indeed, it is necessary to remove the data produced near the ends of the lines, since the intensity drops markedly near the ends and this results in discontinuities. Another cause is that ambient conditions are likely to change between the scan of one stripe and the next, producing a mismatch. Also, a phenomenon known as "bleaching" comes into play: the fluorescence background of the spectrum can burn off or bleach as a function of time or laser power, if the sample is left exposed to the laser beam.

When using a line focus illumination, as described above, the scattered light is usually collected from the sample using a microscope objective lens which has as high a magnification as possible. This maximises the optical collection efficiency. If a sample is to be mapped quickly at a lower resolution, e.g. 50 μm, the data is averaged along the length of the line focus as it is acquired, to get the required resolution. No such averaging takes place in the lateral direction (orthogonal to the line focus). Instead, to quickly obtain a spectral map of the sample the line scan may be repeated in strips, spaced apart by 50 μm in this example. This has the limitation that no data is acquired from the sample between these strips.

SUMMARY OF THE INVENTION

A first aspect of the present invention provides spectroscopic apparatus comprising:
- a source of exciting light arranged to produce a focus on a sample and to generate therefrom a spectrum of scattered light, the focus being moveable relative to the sample;
- a detector comprising a plurality of detector elements, the plurality of detector elements arranged in an array comprising at least one row or column;
- an optical path between the sample and the detector, wherein light scattered from the focus is directed to detector elements within the array;
- wherein the focus is arranged to move, relative to the sample, in a first direction; and
- wherein data concerning light received by the detector from a given region in the sample is accumulated in synchronism with the relative movement of the focus relative to the sample.

The data may be shifted within the detector in a direction corresponding to the first direction, such that said data from a given region of the sample is accumulated in synchronism with the relative movement. Alternatively, the data may be read out of the detector and then combined subsequently such that said data from a given region of the sample is accumulated in synchronism with the relative movement.

In a preferred embodiment, the focus on the sample is a line focus. The line focus and the at least one row or column may be aligned such that light scattered from different portions of the line focus is directed to respective different detector elements within the at least one row or column. The data may pass sequentially along the at least one row or column from one element to the next.

The line focus may be arranged to move, relative to the sample, at least in a longitudinal direction of the line focus. Preferably the line focus extends in said first direction. Synchronously with the relative movement of the line focus over the sample, data may be shifted within the detector so that data from a given point or region of the sample accumulates during the relative movement.

The detector may have multiple detector elements arranged in a two-dimensional array. The detector may comprise, for example, a charge-coupled device.

A spectrum from a point in the focus may be dispersed across the detector in a direction orthogonal to the first direction. A spectrum from any given point in the line focus may be dispersed across the detector in a direction orthogonal to the first direction. An analyser may disperse the spectrum from any given point or region in the line focus across the detector in a direction orthogonal to said at least one row or column. Thus, data representing multiple wavenumbers spread across the spectrum can be acquired simultaneously, in respective rows or columns of the two-dimensional array, while moving the data for each wavenumber along the respective rows or columns, synchronously with the relative movement of the line focus on the sample.

The spectrum may be, for example, a spectrum of Raman scattered light.

Data may be read sequentially from one end of the at least one row or column of detector elements. In one preferred embodiment, data from each element passes sequentially along the at least one row or column from one element to the next. However, that may not always be quite so, for example if the relative movement between the line focus and the sample is more complex and includes a component in a direction transverse to the longitudinal direction, as well as the movement in the longitudinal direction.

The focus may also be arranged to move relative to the sample in a second direction transverse to the first direction, such that the given region from which data accumulates includes points which are spaced from each other in the transverse direction. The line focus may sweep an area of the sample during the relative movement in the second direction. The line focus may sweep said area of the sample bidirectionally. The line focus may move in a zigzag fashion relative to the sample.

The line focus may sweep an entire area of the sample between two boundary lines parallel to the line focus, without omitting any areas between the boundary lines.

A second aspect of the present invention provides spectroscopic apparatus comprising:
- a source of exciting light arranged to produce a line focus on a sample and to generate therefrom a spectrum of scattered light, the line focus and the sample being relatively movable;
- a detector having multiple detector elements arranged in at least one row or column;
- an optical path between the sample and the detector, the line focus and the row or column being aligned such that light scattered from different portions of the line focus is directed to respective different detector elements within the row or column;
- wherein the line focus is arranged to move, relative to the sample, at least in a longitudinal direction of the line focus;
- and that, synchronously with the relative movement of the line focus over the sample, data is shifted within the detector so that data from a given point or region of the sample accumulates during the relative movement.

In another preferred embodiment, the detector may be rotatable through 90°. The detector may then be rotated, when desired, so that the stepping of the data is instead performed in the direction of the dispersion, as described in the above-mentioned U.S. Pat. No. 5,442,438.

A third aspect of the present invention provides spectroscopic apparatus comprising:
- a source of exciting light arranged to produce a focus on a sample and to generate therefrom a spectrum of scattered light, the focus and the sample being relatively movable;
- a detector having multiple detector elements arranged in a two-dimensional array;
- an optical path between the sample and the detector, arranged such that light scattered from the focus is directed to detector elements within the array;
- wherein the focus is arranged to move, relative to the sample, in a first direction;
- wherein data concerning light received by the detector from a given region in the sample 26 is accumulated in synchronism with the relative movement of the focus relative to the sample,
- and wherein the focus is also arranged to move relative to the sample in a second direction transverse to the first, such that the given region from which data accumulates includes points which are spaced from each other in the transverse direction.

BRIEF DESCRIPTION OF THE DRAWINGS

Preferred embodiments of the invention will now be described by way of example, with reference to the accompanying drawings, wherein:

FIGS. 4A, 4B and 4C respectively show the line focus moving relative to the sample, a corresponding shift of charge within a CCD detector, and a spectrum received from one point in the line focus;

DESCRIPTION OF PREFERRED EMBODIMENTS

Figure 1:
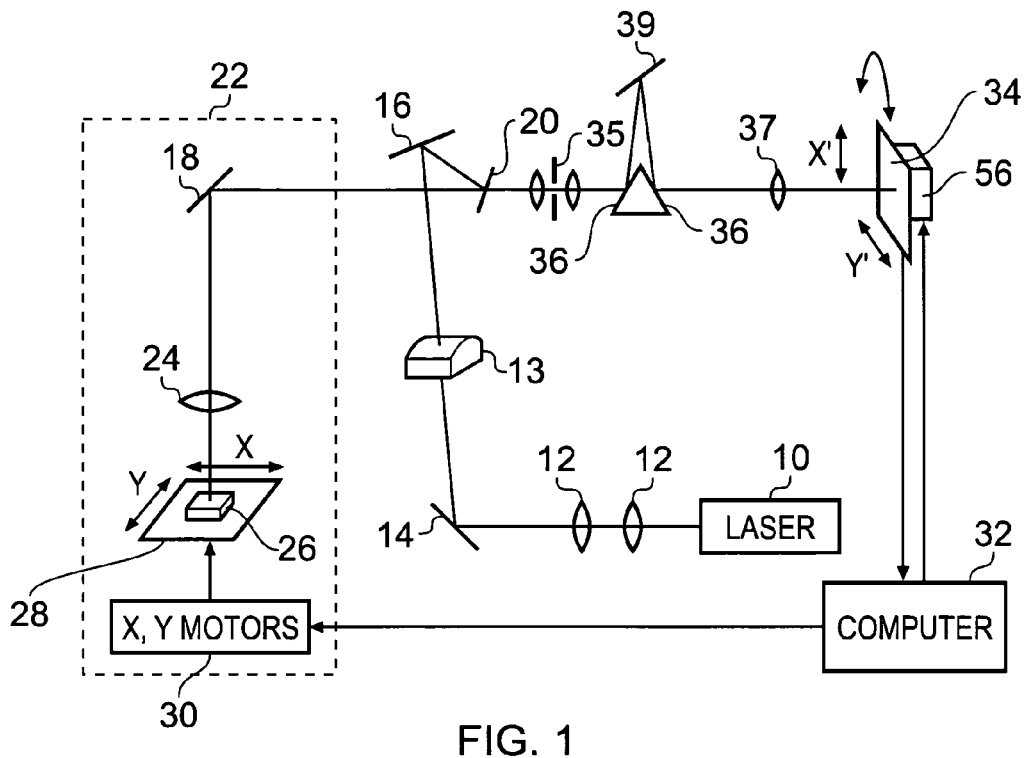
FIG. 1 is a schematic diagram of a first embodiment of spectroscopic apparatus.

Referring to FIG. 1, the spectroscopic apparatus comprises a laser 10 which acts as a source of exciting light. This is passed via a beam expander 12, a cylindrical lens 13, mirrors 14, 16, 18 and a filter 20 into a microscope 22. An objective lens 24 of the microscope 22 focuses the laser beam onto a sample 26 mounted on a stage or table 28. The stage 28 has motors 30 by which it can be moved in directions X and Y, under the control of a computer 32.

The illumination by the exciting laser beam generates scattered light, e.g. Raman scattered light at different frequencies/wavenumbers. This is collected by the microscope objective 24 and directed towards a two-dimensional photodetector array 34. It passes via the mirror 18, filter 20, a slit 35 (which may act confocally to control the depth resolution of the instrument), mirrors 36, a diffraction grating 39 and a focusing lens 37.

The preferred two-dimensional photodetector 34 is a CCD detector. However, other detectors are possible, such as a two-dimensional CMOS photodetector array. The diffraction grating 39 disperses the spectrum of scattered light across the surface of the CCD 34, in a direction X'.

The filter 20 serves a dual purpose. Firstly, it reflects the exciting laser illumination from the laser 10, so as to inject it into the optical path towards the microscope 22 and sample 26. Secondly, it rejects Rayleigh scattered light having the same frequency as the illuminating laser beam and passes only the Raman spectrum of interest towards the CCD detector 34. A variety of different types of dielectric filter having such properties may be used, including for example a holographic filter (which may be placed .at a low angle of incidence to the optical path as shown). If desired, more than one such filter may be provided in series, to improve the rejection of Rayleigh scattered light.

Many of the features of the arrangement described so far are to be found in U.S. Pat. No. 5,442,438, which is incorporated herein by reference for further details.

Rather than merely illuminating one single point at a time on the sample 26 with the laser beam, the cylindrical lens 13 is configured so that a line focus is produced. This then illuminates and excites Raman scattering from multiple points on the sample simultaneously.

Figure 2:
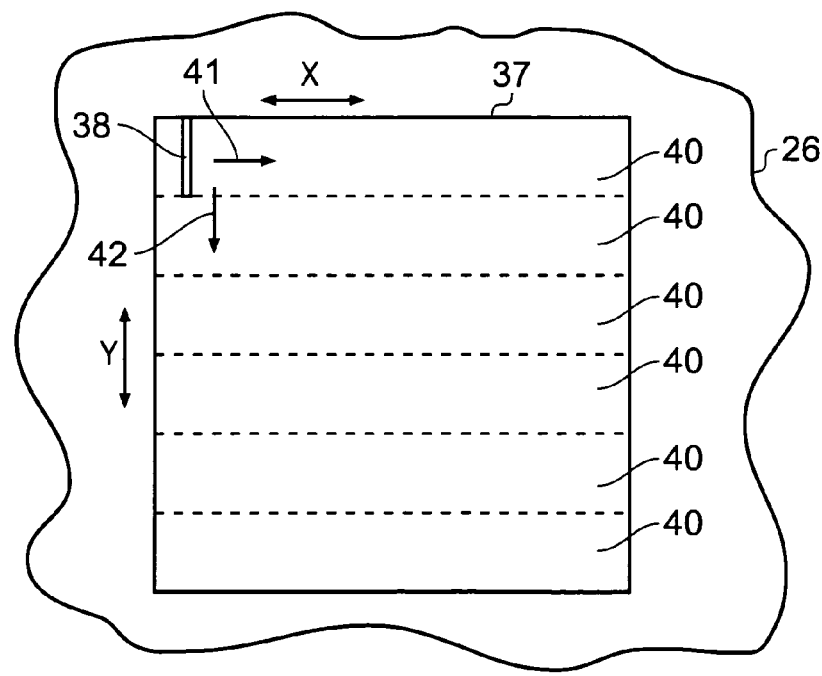
FIG. 2 is a plan view of an area of a sample to be analysed by the apparatus of FIG. 1.

As shown in FIG. 2, typically the area 37 on the sample which is to be analysed has dimensions which are larger than the length of the illuminating line focus 38. Therefore, the line focus 38 is made to perform a raster scan of the area 37. In practice, the relative motion between the line focus of illuminating light and the sample is produced by moving the stage 28 using the motors 30 under the control of the computer 32. Alternatively, however, the illuminating beam itself may be scanned across the surface of a stationary sample, using motorised scanning mirrors to deflect the beams. Again, this is controlled by the computer 32.

In a conventional system, the line focus would first move in the direction X relative to the sample, as indicated by arrow 41, so as to scan a stripe 40. It would then be indexed in the direction Y, as indicated by arrow 42, so as to repeat such scans for successive stripes 40.

However, in the present embodiment, the following method is adopted. Instead of first moving the illuminating line in the X direction orthogonal to its length, it is instead first moved continuously in the Y direction, parallel to its length (i.e. longitudinally). As an alternative to continuous movement, it can instead be moved stepwise, dwelling at each step for a desired exposure period. After each full scan in the Y direction (arrow 42) the line focus is stepped in the X direction (arrow 41) to an adjacent position on the sample, and another scan in the Y direction takes place. This process is repeated until the whole area 37 to be studied has been scanned. This all takes place under the control of the computer 32. It will be appreciated that there are then no stripes 40.

The method used will be further described with reference to FIGS. 4A, 4B and 4C.

FIG. 4A shows a part of the surface of the sample 26, with an imaginary grid of the pixels of the CCD 34 superimposed over it for purposes of discussion. This grid, as shown, covers only a fraction of the area 37 of the sample to be studied. Also shown in FIG. 4A is the line focus 38 of the illuminating laser beam. An arrow 48 shows the direction of movement of the sample relative to the line focus 38, as described above.

FIG. 4B is a representation of the corresponding array of detector elements (pixels) of the CCD detector 34. For each point in the line 38 in FIG. 4A, a Raman spectrum is dispersed in the X' direction along a row of the CCD detector array, for example as illustrated in rows 46. As shown in FIG. 4C, this spectrum may correspond to a substance of interest at the corresponding position in the sample 26. It should be understood that the size of the pixels shown in FIGS. 4A and 4B have been exaggerated, compared to FIG. 4C, and that in real life there are many times this number of pixels.

The exposure of a CCD to light results in the accumulation of charge in each detector element (pixel). This charge represents data and is in proportion to the amount of light it has received during the exposure. Normally, this charge is read out sequentially, after the exposure, by passing it from one detector element to the next. At each of these charge shifting steps, the charge from the pixels at the edge of the array is read into a shift register, from where it is read out and transferred to a computer.

In the present embodiment in FIG. 4B, the charge is shifted in the direction indicated by arrow 50, in a direction Y' corresponding to the direction Y of the movement of the sample (arrow 48, FIG. 4A). It is read one row at a time into a shift register 52, from where it is read out to the computer 32 as indicated at 54. Thus, at any one time during the readout process, the shift register 52 holds the data for one complete spectrum at one point on the line 38.

The shifting of the charge as indicated by arrow 50 takes place simultaneously and synchronously with the scanning of the line 38 in the direction Y as indicated by arrow 48, under the control of the computer 32. The exposure of the CCD to the light continues during this scanning, and charge continues to accumulate as it is shifted from one detector element of the CCD array to the next. Because the charge is shifted synchronously with the relative motion of the sample and the line focus 38, and in the same direction, the light from a given point in the sample 26 continues to accumulate as a spectrum for that point, as shown in FIG. 4C. Such synchronous scanning of the CCD and of the stage continues in the Y direction as indicated by the arrow 42 in FIG. 2, until the line focus has traversed the entire length of the area 37 to be analysed. Then the line focus 38 is stepped to an adjacent position as indicated by arrow 41, and the same procedure takes place until a raster scan has been built up of the entire area 37.

Reference has been made to the accumulation of charge (data) from a point in the sample 26. However, in a lower resolution system, charge may be accumulated from a small area or region of the sample, as described below with reference to FIG. 6.

Figure 3:
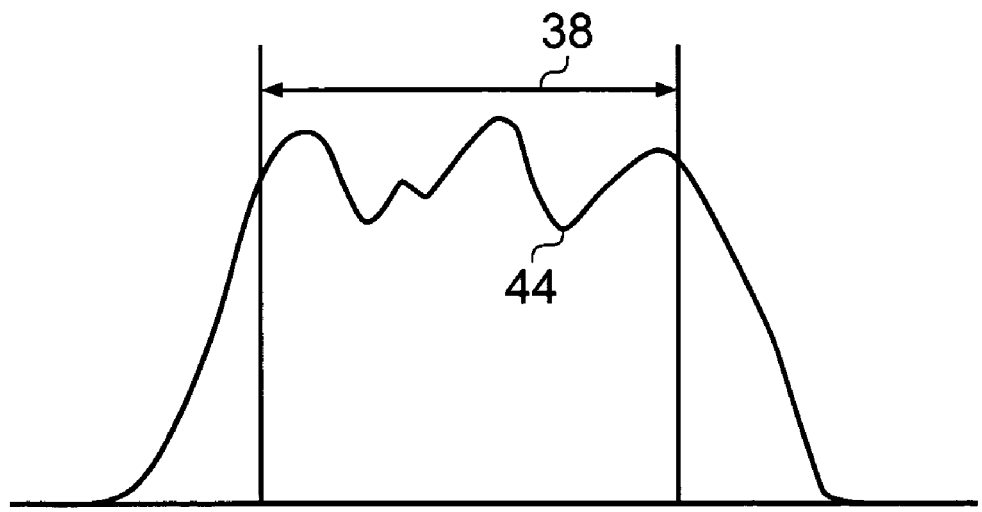
FIG. 3 is a graph showing the variation of intensity of a light beam along a line focus in the apparatus of FIG. 1.

There are several advantages to the technique described above. A first advantage will be explained with reference to FIG. 3. This shows the intensity characteristic of the illuminating laser beam along the length of the line focus 38. Ideally of course, it would be a "top hat" function, having uniform intensity throughout the length of the line 38. In reality, however, this is not possible, and so the intensity curve 44 varies from one position along the line to another. The result, in the conventional technique, is that spectra taken simultaneously from different points along the line have different intensities. This makes it difficult to perform a quantitative analysis which compares the spectra, and to deduce the molecular composition and other information about the various illuminated points along the line. To achieve an appropriate "top hat" function would require a point source laser with a diffractive optical element, which would be expensive.

With the present technique, however, any given point on the sample 26 is illuminated successively by light from each position within the length of the line focus 38. Thus, each point on the sample experiences illumination from each of the differing intensities shown by the curve 44 in FIG. 3. The effect is to integrate all these intensities so that the differences between them have no effect.

A second advantage is that there is a smooth transition of the illuminating line 38 throughout the Y direction of the area 37, so that no differences are perceived between different stripes 40 as in the prior technique described. The data is acquired seamlessly and there is no need to try to stitch together data at the edges of strips 40.

A third advantage is that should there be any differences between the responses of different detector elements of the CCD array 34, or variations in instrument transfer function between different pixels, then these too are integrated over the whole area of the sample. So this has no effect on the resulting output as it would in the prior art, and facilitates accurate analysis of the results. Indeed, even a defective detector element which gave no signal output could be tolerated.

A fourth advantage is that scanning a line focus results in faster mapping of the sample area, compared to point-by-point scanning. In cases where a large sample area is to be mapped with only a short exposure time at each point, then it can be shown that the present method is even faster than the previously known method of line focus scanning.

It will be noted that the direction 50 of the charge shift in FIG. 4B is orthogonal to the prior art synchronous scanning method described with reference to FIG. 8 of U.S. Pat. No. 5,442,438. In that prior method, the charge is shifted in the direction of the spectral dispersion, corresponding to the direction X' in FIG. 4B of the present application. Thus, the present invention achieves a different effect from that described in the prior patent.

The computer 32 is programmed to control the shifting of the charge synchronously with the movement of the motors 30. It also controls the readout 54 from the shift register 52 and the resulting data acquisition. If it is desired to produce the relative motion of the line focus 38 and the sample by scanning the light beam across a stationary sample, the computer 32 may control the scanning mirrors which cause the scanning of the illuminating beam and which collect the scattered light from a sample.

If it is desired to have the ability to provide the synchronous scanning described in the embodiment above, as well as the synchronous scanning in the spectral dimension as described in U.S. Pat. No. 5,442,438, then there are several possibilities.

One such possibility is to utilise a CCD detector array which has the ability to shift charges in both the X' and Y' directions, to respective shift registers on orthogonal edges of the array. The charges can then be shifted in the Y' direction as described above, or in the X' direction if it is desired to perform the method according to the prior patent.

Alternatively, as shown in FIG. 1, the CCD detector 34 may be mounted on an optional rotatable mounting 56. This is indexable through 90°, between a position in which it can perform the method described above, and an orthogonal position in which it can perform the method of the prior patent. To ensure repeatable repositioning of the detector at each of the two orthogonal positions, the rotatable mounting may comprise kinematic mounts at each of the two indexed positions. If desired, the rotatable mounting 56 may be motorised and under control of the computer 32 to change the scanning mode from one position to the other.

Figure 5:
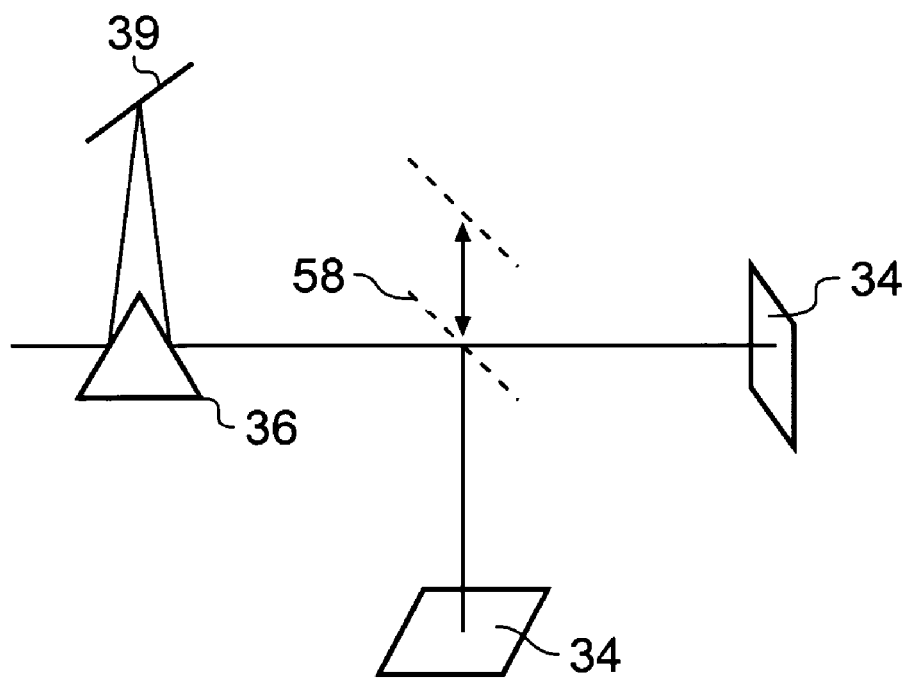
FIG. 5 shows an alternative arrangement of part of the apparatus of FIG. 1.

Alternatively, as shown in FIG. 5, two CCD detectors 34 may be used. One is set up to perform the technique as described above, while the other is set up to perform the technique of the prior patent. The light may be switched from one detector to the other by a movable mirror 58, which can be moved into and out of the beam path. Again, this may be motorised and under the control of the computer 32, if desired. Further methods of switching between one CCD detector and another are possible, such as mounting both of them side-by-side on a linear slide so that the desired one can be positioned in the optical path.

A further technique according to the present invention will now be described with reference to FIG. 6. It is similar to the techniques described above, except as follows. It is intended for gathering data from the sample at a lower resolution R in the X direction than the above techniques, e.g. 50 μm.

Figure 6:
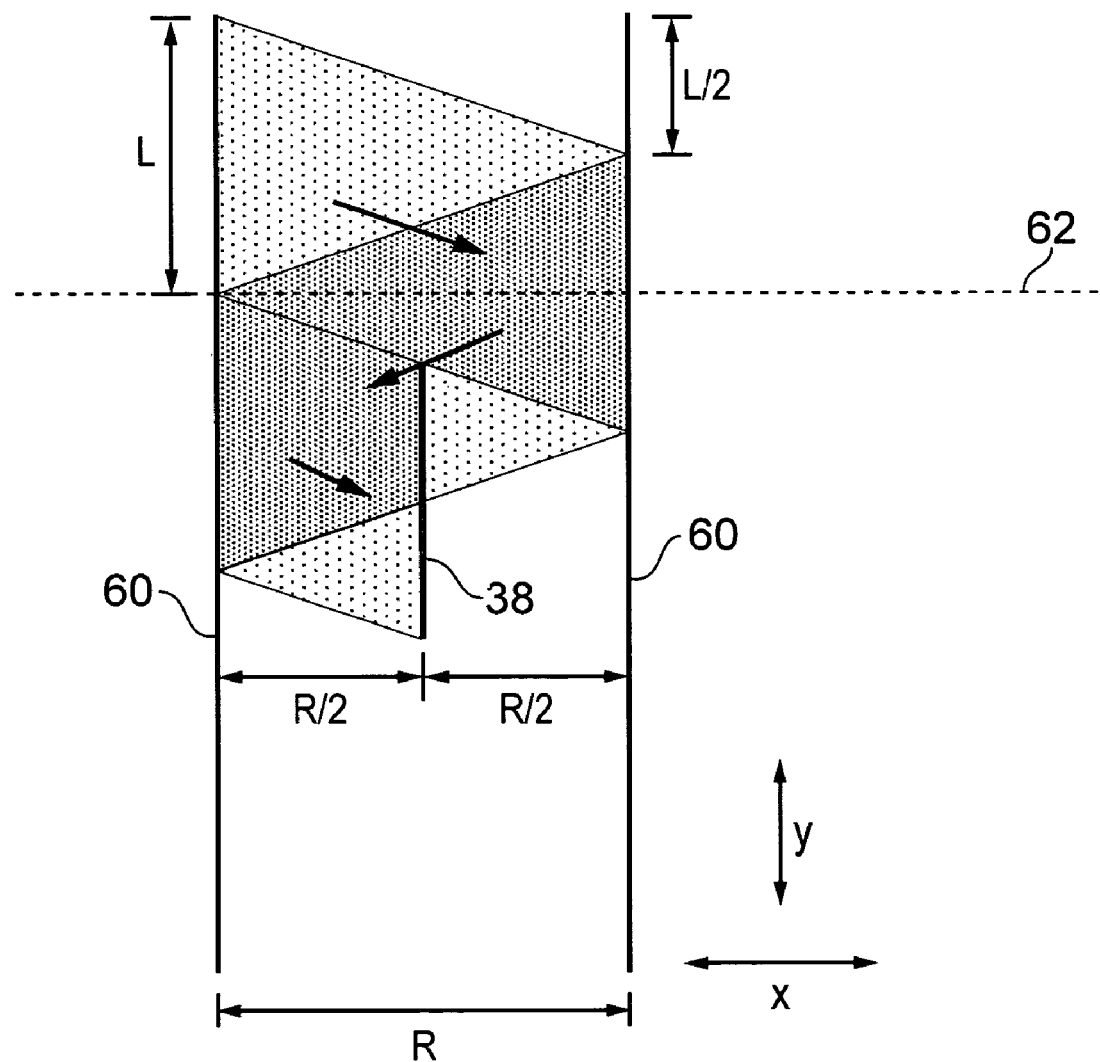
FIG. 6 is a plan view of an area of a sample, showing a preferred technique of the present invention.

FIG. 6 shows two longitudinal scanning boundary lines 60, parallel to the line focus 38 and spaced apart by the lateral resolution R (50 μm). The computer 32 is programmed to move the X,Y motors 30 of the stage 28 simultaneously, so that the relative motion between the sample and the line focus 38 proceeds in a zigzag between the two boundary lines, as shown in FIG. 6. Thus, in the same time that it takes the Y motor of the stage to move the sample by the length of the line 38, the X motor of the stage moves it laterally by a distance R/2 from a central position to one of the boundary lines 60, reverses direction and moves it by a distance R to the other boundary line, and then moves it back to the central position. This ensures that the entire area between the boundary lines 60 is swept by the line focus 38.

This zigzag motion is repeated between the boundary lines 60 over the entire length in the Y direction of the area 37 to be scanned (arrow 42 in FIG. 2). The stage is then stepped in the X direction by the distance R (arrow 41 in FIG. 2) and the zigzag motion is repeated. In this way, the entire area 37 is covered by the scan.

As previously, the spectra from the various points in the line 38 are dispersed in the X' direction across the CCD 34. The charges accumulating in the CCD 34, representing these spectra, are shifted in the Y' direction simultaneously and synchronously with the Y movement of the stage 28, and are read out to the computer 32 via the output shift register 52.

Because of the lateral zigzag movement of the line focus relative to the sample, the data of each collected spectrum is averaged over the lateral resolution distance R. If no binning (combination of the charges from adjacent pixels) is performed as the data is read out via the register 52, then the resulting data would be the equivalent of a wide spot (one pixel in the Y direction and n pixels in the X direction, where n is the number of pixels in the distance R). However, binning may be applied, under the control of the computer 32, to vary the resolution in the Y direction. The data from these wide spots is then added together, to give resolutions of varying aspect ratios, up to and beyond square.

As shown in FIG. 6, the line 38 scans each part of the sample with a bidirectional pass. This helps to ensure that sampling of the area is performed evenly. The initial data collected over the first line length L, above a line 62, is not bidirectional, and considered as a prescan, which is discarded.

The advantage of this technique is that data can be obtained representing the entire area of the sample, at any desired resolution, without omitting any areas between the boundary lines of the scan. Thus, a small particle of a substance will influence the averaged results, whereas if scanning were to proceed in sparse narrow strips corresponding to the resolution R, it could be missed.

Rather than the CCD 34, other detectors are possible, such as a two-dimensional CMOS photodetector array. In this case, transfer of charge within the detector chip itself is not possible, so the data for multiple exposures is read out of the detector, and then combined and manipulated subsequently within the computer 32. The computer is programmed to combine the data in the same manner as if it had been accumulated within the detector chip as described above. That is, the data concerning light from a given region in the sample 26 is accumulated in synchronism with the scan as data for that region, even though collected from different pixels of the detector as the scan progresses. A high-speed detector chip should be used for best results, and a higher level of read-out noise may be suffered.

The invention claimed is:

1. A spectroscopic apparatus comprising:
a source of exciting light arranged to produce a focus on a sample and to generate therefrom scattered light, the focus being moveable relative to the sample;
a detector comprising a plurality of detector elements, the plurality of detector elements arranged in an array comprising at least one row or column;
an optical path between the sample and the detector, wherein light scattered from the focus is directed to detector elements within the array;
a dispersive device in the optical path for dispersing the scattered light into a spectrum;
wherein the focus is arranged to move, relative to the sample, in a first direction; and
wherein data concerning light received by the detector from a given region in the sample is accumulated in synchronism with the relative movement of the focus relative to the sample.

2. Spectroscopic apparatus according to claim 1, wherein data is shifted within the detector in a direction corresponding to the first direction, such that said data from a given region of the sample is accumulated in synchronism with the relative movement.

3. Spectroscopic apparatus according to claim 2 wherein the data is passed sequentially along the at least one row or column from one detector element to the next.

4. Spectroscopic apparatus according to any of claim 1, wherein data is read sequentially from the detector elements of the at least one row or column.

5. Spectroscopic apparatus according to claim 1, wherein the detector comprises a charge-coupled device.

6. Spectroscopic apparatus according to claim 1, wherein data is read out from the detector and combined subsequently such that said data from a given region of the sample is accumulated in synchronism with the relative movement of the focus relative to the sample.

7. Spectroscopic apparatus according to claim 1, the detector having a plurality of detector elements arranged in a two-dimensional array, wherein the dispersive device is arranged for dispersing the spectrum from a point in the focus across the detector in a direction orthogonal to the first direction.

8. Spectroscopic apparatus according to claim 1, wherein the focus on the sample is a line focus.

9. Spectroscopic apparatus according to claim 8, wherein the line focus extends in said first direction.

10. Spectroscopic apparatus according to claim 8, wherein the line focus is aligned with the at least one row or column of the detector elements, such that light scattered from different portions of the line focus is directed to respective different detector elements within the row or column.

11. Spectroscopic apparatus according to claim 10 wherein, synchronously with the relative movement of the line focus to the sample, data is shifted within the detector so that data from a given point or region of the sample accumulates during the relative movement.

12. Spectroscopic apparatus according to claim 9, the detector having multiple detector elements arranged in a two-dimensional array, wherein a the dispersive device is arranged for dispersing the spectrum from any given point in the line focus across the detector in a direction orthogonal to the first direction.

13. Spectroscopic apparatus according to claim 12, wherein data representing multiple wavenumbers spread across the spectrum is acquired simultaneously, in respective rows or columns of the two-dimensional array, while moving the data for each wavenumber along the respective columns or rows, synchronously with the relative movement of the line focus on the sample.

14. A spectroscopy apparatus comprising:
a source of existing light arranged to produce a line focus on a sample and to generate therefrom a spectrum of scattered light, the line focus being moveable relative to the sample;
a detector comprising a plurality of detector elements, the plurality of detector elements arranged in a two-dimensional array;
an optional path between the sample and the detector, wherein light scattered from the line focus is directed to detector elements within the array;
wherein the line focus extends in a first direction and is arranged to move, relative to the sample, in the first direction, the spectrum from any given point in the line focus being dispersed across the detector in a direction orthogonal to the first direction;
wherein data concerning light received by the detector from a given region in the sample is accumulated in synchronism with the relative movement of the focus relative to the sample; and
wherein the detector is rotatable through 90°, whereby the detector may be rotated, when desired, so that shifting of the data may be performed in the direction of the dispersion of the spectrum.

15. Spectroscopic apparatus according to claim 1, the detector having multiple detector elements arranged in a two-dimensional array.

16. Spectroscopic apparatus according to claim 15 wherein the focus is also arranged to move relative to the sample in a second direction transverse to the first direction, such that the given region from which data accumulates includes points which are spaced from each other in the transverse direction.

17. Spectroscopic apparatus according to claim 16, wherein the focus is a line focus and the line focus sweeps an area of the sample during the relative movement in the second direction.

18. Spectroscopic apparatus according to claim 17 wherein the line focus sweeps said area of the sample bidirectionally.

19. Spectroscopic apparatus according to claim 1, wherein the focus moves in a zigzag fashion relative to the sample.

20. Spectroscopic apparatus according to claim 17, wherein the line focus sweeps an entire area of the sample between two boundary lines parallel to the line focus, without omitting any areas between the boundary lines.

21. Spectroscopic apparatus comprising:
a source of exciting light arranged to produce a line focus on a sample and to generate therefrom a spectrum of scattered light, the line focus and the sample being relatively movable;
a detector having multiple detector elements arranged in at least one row or column;
an optical path between the sample and the detector, the line focus and the row or column being aligned such that light scattered from different portions of the line focus is directed to respective different detector elements within the row or column;
wherein the line focus is arranged to move, relative to the sample, at least in a longitudinal direction of the line focus;

and that, synchronously with the relative movement of the line focus over the sample, data is shifted within the detector so that data from a given point or region of the sample accumulates during the relative movement.

22. Spectroscopic apparatus comprising:
a source of exciting light arranged to produce a focus on a sample and to generate therefrom a spectrum of scattered light, the focus and the sample being relatively movable;
a detector having multiple detector elements arranged in a two-dimensional array;
an optical path between the sample and the detector, arranged such that light scattered from the focus is directed to detector elements within the array;
wherein the focus is arranged to move, relative to the sample, in a first direction;
wherein data concerning light received by the detector from a given region in the sample is accumulated in synchronism with the relative movement of the focus relative to the sample,
and wherein the focus is also arranged to move relative to the sample in a second direction transverse to the first, such that the given region from which data accumulates includes points which are spaced from each other in the transverse direction.

* * * * *